US006607901B1

(12) United States Patent
Schaffer et al.

(10) Patent No.: US 6,607,901 B1
(45) Date of Patent: Aug. 19, 2003

(54) ALKALINE ALPHA-GALACTOSIDASE

(75) Inventors: Arthur Schaffer, Hashmonaim (IL); Gao Zhifang, Beit Dagan (IL)

(73) Assignee: State of Israel-Ministry of Agriculture, Volcani Research Center, Beitdagan (IL)

( * ) Notice: Subject to any disclaimer, the term of this patent is extended or adjusted under 35 U.S.C. 154(b) by 0 days.

(21) Appl. No.: 09/744,086

(22) PCT Filed: Jul. 19, 1999

(86) PCT No.: PCT/IL99/00395
§ 371 (c)(1),
(2), (4) Date: Apr. 25, 2001

(87) PCT Pub. No.: WO00/05351
PCT Pub. Date: Feb. 3, 2000

(30) Foreign Application Priority Data

Jul. 20, 1998 (IL) .................................................. 125423

(51) Int. Cl.$^7$ ............................ C12N 9/00; C12N 9/24; C12N 9/40; C12Q 1/00; C12P 1/00; C12P 19/34; C12P 19/20

(52) U.S. Cl. .............................. 435/208; 435/4; 435/14; 435/183; 435/200; 435/91.53; 435/96; 435/262

(58) Field of Search ........................... 435/4, 183, 200, 435/208, 262, 14, 41, 91.53, 96; 536/23.2

(56) References Cited

FOREIGN PATENT DOCUMENTS

| WO | WO 95/06478 | 3/1995 |
|---|---|---|
| WO | WO 95/07088 | 3/1995 |

OTHER PUBLICATIONS

Margolles–Clark et al., "Three alpha–galactosidase genes of *Trichoderma reesi* cloned by expression in yeast", Eur. J. Biochemistry, 240:104–111, 1996.
Bulpin, P.V., et al., "Development of a biotechnological process for the modification of galactomannan polymers with plant alpha–galactosidase", Carbohydrate Polymers 12:155–168, 1990.
Suzuki et al., "Studies on the decomposition of raffinose by alpha–galactosidase of mold" Agr. Biol. Chem., 33:501–513, 1969.
Thananunkal et al., "Degradation of raffinose and stachyose in soybean milk by alpha–galactosidase from *Mortierella vinacea*" Jour. Food Science, 41:173–175, 1976.
Harpaz et al., "Studies on B–antigenic sites of human erythrocytes by use of coffee bean alpha–galactosidase", Archives of Biochemistry and Biophysics, 170:676–683, 1975.
Zhu et al. "Characterization of recombinant alpha–galactosidase for use in seroconversion from blood group B to O of human erythrocytes", Archives of Biochemistry and Biophysics, 327:324–329, 1996.

Keller F. and Pharr D. M., "Metabolism of Carbohydrates in Sinks and Sources: Galactosyl–Sucrose Oligosaccharides", In: Zamski, E. and Schaffer, A.A. (eds.) Photoassimilate Partitioning in Plants and Crops: Source–Sink Relationships, ch. 7, pp. 168–171, 1996, Marcel Dekker Publ., N.Y.
Talbot, G. and Sygusch, J., "Purification and characterization of thermostable b–mannanase and alpha–galactosidase from *Bacillus stearothermophilus*", Applied and Environmental Microbiology, 56:3503–3510, 1990.
Schmid and Schmitt, "Raffinose metabolism in *Escherichia coli* K12: purification and properties of a new alpha–galactosidase specified by a transmissible plasmid", Eur. J. Biochemistry, 67:95–104, 1976.
Hashimoto, H. et al., "Purification and some properties of alpha–galactosidase from *Pseudomonas fluorescens* H–601", Agric. Biol. Chem., 55:2831–2838, 1991.
del Campillo, E., et al., "Molecular properties of the enzymic phytohemagglutinin of mung bean", J. Biol. Chem. 256:7177–7180, 1981.
Schaffer, A.A., Madore, M. and Pharr, D.M., In: Zamski, E. and Schaffer, A.A. (eds.) Photoassimilate Partitioning in Plants and Crops: Source–Sink Relationships, ch. 31, pp. 729–758, 1996, Marcel Dekker Publ., N.Y.
P.–R. Gaudreault and J. A. Webb, "Alkaline alpha–galactosidase in leaves of *Cucurbita pepo*", Plant Sci. Lett. 24, 281–288, 1982.
Pharr and Hubbard. Melons: Biochemical and Physiological Control of Sugar Accumulation, In: Encyclopedia of Agricultural Science, vol. 3, pp. 25–37, Arntzen, C.J., et al., eds. Academic Press, N.Y., 1994.
Irving et al., "Changes in carbohydrates and carbohydrate metabolizing enzymes during the development, maturation and ripening of buttercup squash, *Cucurbita maxima* D. Delica", J. Amer. Soc. Hort. Sci., 122: 310–314, 1997.
Chrost and Schmitz, "Changes in soluble sugar and activity of alpha–galactosidase and acid invertase during muskmelon (*Cucumis melo* L.) fruit development". J. of Plant Physiology, 151:41–50, 1977.
Courtois and Petek, "Alpha–galactosidase from coffee bean", Methods in Enzymology, vol. 8:565–571, 1966.
Dey, P.M. and Pridham, J.B., "Purification and properties of alpha–galactosidase from *Vicia faba* seeds", Bioch. J., 113:49–54, 1969.
Bachmann et al., "Metabolism of the raffinose family oligosaccharides in leaves of *Ajuga reptens* L.", Plant Physiology 105:1335–1345, 1994.

(List continued on next page.)

*Primary Examiner*—Rececca E. Prouty
*Assistant Examiner*—Manjunath N. Rao
(74) *Attorney, Agent, or Firm*—G.E. Ehrlich (1995) Ltd.

(57) ABSTRACT

An enzyme isolated from an organism that metabolizes alpha-galactosyl containing saccharides, comprising an alpha-galactosidase (E.C. 3.2.1.22, alpha-D-galactoside galatohydrolase) with optimal activity in the neutral to alkaline pH range, and which hydrolyzes a variety of alpha-galactose containing saccharides, in particular raffinose. The enzyme is preferably a protein monomer and an ex-alpha-galactosidase.

18 Claims, 10 Drawing Sheets

OTHER PUBLICATIONS

Madore, M., "Catabolism of raffinose family oligosaccharides by vegetative sink tissues", In: Carbon Partitioning and Source–Sink Interactions in Plants, Madore, M. and Lucas, W.J. (eds.) pp. 204–214, 1995, American Society of Plant Physiologists, Maryland.

Smart and Pharr, "Characterization of alpha–galactosidase from cucumber leaves", Plant Physiology, 66:731–734, 1980.

Pressey, R., "Tomato Alpha–Galactosidase: Conversion of Human Type B Erythrocytes to Type 0" Phytochemistry 23:55–58, 1984.

P.–R. Gaudreault and J. A. Webb, "Alkaline alpha–galactosidase activity and galactose metabolism in the family Cucurbitaceae", Plant Science, 45, 71–75, 1986.

P.–R. Gaudreault and J. A. Webb, "Partial purification and properties of an alkaline alpha–galactosidase from mature leaves of *Cucurbita pepo*", Plant Physiol., 71, 662–668, 1983.

Gao Z, Schaffer AA: "A novel alkaline alpha–galactosidase from melon fruit with a substrate preference for raffinose" Plant Physiology, vol. 119, No. 3, Mar. 1999, pp. 979–987.

Goldstein et al., "Group B erythrocytes enzymatically converted to group O survive normally in A, B, and O individuals" Science, 215:168–170, 1982.

Purified alkaline alpha-galactosidase forms I (79 kDA) and II (92 kDA) in 8% SDS-PAGE

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial sequence
<220> FEATURE:
<223> OTHER INFORMATION: Peptide derived from proteolytic degredation
      for protein identification

<400> SEQUENCE: 1

Glu Tyr Pro Ile Gln Ser Pro Gly Asn Val Ser Asn Leu
1               5                   10

<210> SEQ ID NO 2
<211> LENGTH: 9
<212> TYPE: PRT
<213> ORGANISM: Artificial sequence
<220> FEATURE:
<223> OTHER INFORMATION: Peptide derived from proteolytic degredation
      for protein identification
<220> FEATURE:
<221> NAME/KEY: misc_feature
<222> LOCATION: (7)..(7)
<223> OTHER INFORMATION: Arginine or Leucine

<400> SEQUENCE: 2

Asp Ile Ser Leu Thr Glu Xaa Val Thr
1               5

<210> SEQ ID NO 3
<211> LENGTH: 17
<212> TYPE: PRT
```

```
-continued

<213> ORGANISM: Artificial sequence
<220> FEATURE:
<223> OTHER INFORMATION: Peptide sequence derived from N'- sequencing
      of alkaline alpha-galactosidase I

<400> SEQUENCE: 3

Thr Val Gly Ala Gly Ile Thr Ile Ser Asp Ala Asn Leu Thr Val Leu
1               5                   10                  15

Gly
```

ALKALINE ALPHA-GALACTOSIDASE

FIELD OF THE INVENTION

The present invention relates generally to enzymes for hydrolysis of sugars and particularly to an alkaline alpha-galactosidase which hydrolyzes a broad spectrum of galactosyl-saccharides such as melibiose, raffinose and stachyose and guar gum, at neutral to alkaline pH conditions.

BACKGROUND OF THE INVENTION

The enzyme alpha-galactosidase (E.C. 3.2.1.22; alpha-D-galactoside galactohydrolase) catalyzes the hydrolysis of the terminal linked alpha-galactose moiety from galactose-containing oligosaccharides. These include, for example, the naturally occurring disaccharide melibiose (6-O-alpha-D-galactopyranosyl-D-glucose), the trisaccharide raffinose (O-alpha-D-galactopyranosyl-(1-6)-O-alpha-D-glucopyranosyl-(1-2)-beta-D-fructofuranoside) and the tetrasaccharide stachyose (O-alpha-D-galactopyranosyl-(1-6)-O-alpha-D-galactopyranosyl-(1-6)-O-alpha-D-glucopyranosyl-(1-2)-beta-D-fructofuranoside). Alpha-galactosidases have potential use in various applications, and some examples are described by Margolles-Clark et al. ("Three alpha-galactosidase genes of Trichoderma reesi cloned by expression in yeast", Eur. J. Biochemistry, 240:104–111, 1996). They may hydrolyze alpha-galactose residues from polymeric galactomannans, such as in guar gum; modification of guar gum galactomannan with alpha-galactosidase has been used to improve the gelling properties of the polysaccharide (Bulpin, P. V., et al., "Development of a biotechnological process for the modification of galactomannan polymers with plant alpha-galactosidase", Carbohydrate Polymers 12:155–168, 1990). Alpha-galactosidase can hydrolyze raffinose from beet sugar syrup, which can be used to facilitate the sugar crystallization from molasses, since the raffinose presents an obstacle to the normal crystallization of beet sugar (Suzuki et al., "Studies on the decomposition of raffinose by alpha-galactosidase of mold" Agr. Biol. Chem., 33:501–513, 1969). Additionally, alpha-galactosidase can be used to hydrolyze stachyose and raffinose in soybean milk, thereby reducing or eliminating the undesirable digestive side effects which are associated with soybean milk (Thananunkal et al., "Degradation of raffinose and stachyose in soybean milk by alpha-galactosidase from Mortierella vinacea" Jour. Food Science, 41:173–175, 1976). The enzyme can also remove the terminal alpha-galactose residue from other glycans, such as the erythrocyte surface antigen conferring blood group B specificity. This has potential medical use in transfusion therapy by converting blood group type B to universal donor type O (Harpaz et al. "Studies on B-anticenic sites of human erythrocytes by use of coffee bean alpha-galactosidase", Archives of Biochemistry and Biophysics, 170:676–683, 1975, and by Zhu et al. "Characterization of recombinant alpha-galactosidase for use in seroconversion from blood group B to O of human erythrocytes", Archives of Biochemistry and Biophysics, 327:324–329, 1996).

Plant alpha-galactosidases from numerous sources have been studied and multiple forms of the enzyme have been described, such as in Keller F. and Pharr D. M., "Metabolism of Carbohydrates in Sinks and Sources: Galactosyl-Sucrose Oligosaccharides", In: Zamski, E. and Schaffer, A. A. (eds.) Photoassimilate Partitioning in Plants and Crops: Source-Sink Relationships, ch. 7, pp. 168–171, 1996, Marcel Dekker, Publ., N.Y. These can be classified into two broad groups, acid or alkaline, according to the pH at which they show optimal activity. Practically all studies of alpha-galactosidases have dealt with the acidic forms of the enzyme and these play important roles in seed development and germination. Alpha-galactosidases with optimal activity at alkaline pH are uncommon in eucaryotic organisms.

Alpha-galactosidases which show preferred activity to the disaccharide melibiose are often referred to as melibiases. These may have optimal activity at alkaline pH but are relatively specific to melibiose, with only little activity and low affinity to the trisaccharide raffinose. In addition, they characteristically function as a multimeric protein. For example, the bacterial alpha-galactosidase that has been described from Bacillus stearothermophilus (Talbot, G. and Sygusch, J., "Purification and characterization of thermostable b-mannanase and alpha-galactosidase from Bacillus stearothermophilus", Applied and Environmental Microbiology, 56:3503–3510, 1990) has over a 15-fold higher activity with melibiose, as compared to raffinose and functions as a trimer. The alpha-galactosidase described from Escherichia coli K12 similarly has only about 4% of the activity with raffinose as compared to melibiose, with Km values of 60 mM and 3.2 mM, respectively, in addition to functioning as a tetrameric protein (Schmid and Schmitt, "Raffinose metabolism in Escherichia coli K12: purification and properties of a new alpha-galactosidase specified by a transmissible plasmid", Eur. J. Biochemistry, 67:95–104, 1976). Similarly, the enzyme from Pseudomonas fluorescens H-601 (Hashimoto, H. et al., "Purification and some properties of alpha-galactosidase from Pseudomonas fluorescens H-601", Agric. Biol. Chem., 55:2831–2838, 1991) has relative Km values for raffinose and melibiose of 17 and 3.2 mM, respectively, and functions as a tetramer.

There are obvious advantages to the use of a monomer protein with the desired enzyme activity, as compared to multimeric proteins. This has clearly been shown, for example, with the alpha-galactosidases from mung bean seeds (del Campillo, E., et al., "Molecular properties of the enzymic phytohemagglutinin of mung bean", J. Biol. Chem. 256:7177–7180, 1981) in which the retrameric form of the enzyme disassociated into the monomeric form during storage, and this was accompanied by loss of activity.

The galactosyl-sucrose sugars, stachyose and raffinose, together with sucrose, are the primary translocated sugars in the phloem of cucurbits, which includes muskmelons, pumpkins and cucumber. The very low concentrations of raffinose and stachyose in fruit tissues of muskmelon suggest that galactosyl-sucrose unloaded from phloem is rapidly metabolized, with the initial hydrolysis by alpha-galactosidase, as described in "Cucurbits", Schaffer, A. A., Madore, M. and Phan, D. M., In : Zamski, E. and Schaffer, A. A. (eds.) Photoassimilate Partitioning in Plants and Crops: Source-Sink Relationships, ch. 31, pp. 729–758, 1996, Marcel Decker Publ., N.Y.

P.-R. Gaudreault and J. A. Webb have described in several publications, (such as "Alkaline alpha-galactosidase in leaves of Cucurbita pepo", Plant Sci. Lett. 24, 281–288, 1982, "Partial purification and properties of an alkaline alpha-galactosidase from mature leaves of Cucurbita pepo", Plant Physiol., 71, 662–668, 1983, and "Alkaline alpha-galactosidase activity and galactose metabolism in the family Cucurbitaceae", Plant Science, 45, 71–75, 1986), a novel alpha-galactosidase purified from young leaves of Cucurbita pepo, that has an optimal activity at alkaline conditions (pH 7.5). In addition to the alkaline alpha-galactosidase, they also reported three acid forms of the enzyme, and distinct substrate preferences were found for the acid and alkaline forms. Raffinose was found to be the preferred substrate of the acidic forms. The alkaline form had high affinity (Km=4.5 mM) and high activity (1.58 μmol galactose formed per min per mg protein) only with stachyose. It had low affinity for (Km=36.4 mM) and low activity (0.14 μmol galactose formed per min. per mg protein) toward the trisaccharide raffinose and hydrolyzed melibiose very slowly and therefore affinity and activity on that sugar was not calculated. Thus, this previously reported alkaline alpha-galactosidase can be described as having activity at alkaline pH but with only a narrow spectrum of substrates.

A further characteristic of the alkaline alpha-galactosidase from young leaves of *Cucurbita pepo* is that alpha-D-galactose, the product of the enzymatic reaction, is a strong inhibitor of the enzyme's activity (Gaudreault and Webb, 1983), similar to many of the acid alpha-galactosidases. Geaudreault and Webb calculated that 6.4 mM galactose reduced the reaction velocity of alkaline alpha-galactosidase by 50%, in a reaction mixture containing 7.5 mM pNPG at pH 7.5. Such an inhibition by the product of the reaction (termed "product inhibition"), generally has important physiological significance in metabolism.

Gaudreault and Webb (among others) have suggested that the alkaline alpha-galactosidase, as the initial enzyme in the metabolic pathway of stachyose and raffinose catabolism, was important in phloem unloading and catabolism of transported stachyose in the young cucurbit leaf tissue. It is likely that alpha-galactosidase similarly plays an important role in the carbohydrate partitioning in melon plants, and may have possible functions for phloem unloading in fruits of muskmelon. Recently, alpha-galactosidase activity at alkaline pH has been observed in other cucurbit tissue, such as cucumber fruit pedicels, young squash fruit and young melon fruit. Results obtained by Pharr and Hubbard ("Melons: Biochemical and Physiological Control of Sugar Accumulation, In: Encyclopedia of Agricultural Science, vol. 3, pp. 25–37, Arntzen, C. J., et al., eds. Academic Press, N.Y., 1994) led them to suggest that stachyose degradation by alpha-galactosidase took place within pedicels of fruit of *Cucumis sativus*, especially in the regions where the pedicel joins the fruit. Recently, Irving et al. ("Changes in carbohydrates and carbohydrate metabolizing enzymes during the development, maturation and ripening of buttercup squash, *Cucurbita maxima* D. Delica", J. Amer. Soc. Hort. Sci., 122: 310–314, 1997) reported the developmental changes in alpha-galactosidase activities, measured at acid and alkaline pH, in buttercup squash (*Cucurbita maxima*) fruit. They found that at anthesis, alkaline activity was higher than activity at acid pH and that both activities declined during fruit development. Chrost and Schmitz ("Changes in soluble sugar and activity of alpha-galactosidase and acid invertase during muskmelon (*Cucumis melo L.*) fruit development". J. of Plant Physiology, 151:41–50, 1977) reported approximately similar activities of alpha-galactosidase at acid and alkaline pH in *Cucumis melo* fruit at the anthesis stage.

However, all of these studies were carried out using the non-specific artificial substrate, p-nitrophenyl alpha-galactopyranoside (pNPG), which indicates alpha-galactosidase activity but does not reflect either the physiological role of the particular enzyme forms, or, more importantly, the substrate specificity of the particular enzyme. Thus, the prior art gives no reason to indicate that the above described alkaline alpha-galactosidase enzyme activity in the fruit pedicel or fruit tissue, which were assayed with pNPG, might in any way be novel.

Furthermore, it is well established that the artificial substrate pNPG often indicates a higher pH optimum for alpha-galactosidase activity than that which is observed with the natural substrates. For example, Courtois and Petek ("Alpha-galactosidase from coffee bean", Methods in Enzymology, vol. 8:565–571, 1966) state that "With alpha-phenylgalactoside (pNPG) one observes a pH optimum at pH 3.6, and a second more pronounced peak at pH 6.1. Toward other substrates (melibiose, raffinose, planteose and stachyose) the pH curve is flatter, with a maximum between 3.6 and 4.0". Similar results were observed for the alpha-galactosidase of *Vicia faba* seeds (Dey. P. M. and Pridham, J. B., "Purification and properties of alpha-galactosidase from *Vicia faba* seeds", Bioch. J., 113:49–54, 1969).

While it had been thought that alkaline alpha-galactosidase may be confined to the cucurbit family, which includes the above mentioned squash, cucumber and melon plants, it has recently been shown by Bachmann et al. ("Metabolism of the raffinose family oligosaccharides in leaves of *Ajuga reptens L.*", Plant Physiology 105:1335–1345, 1994) that *Ajuga reptens* plants (common bugle), a stachyose translocator from the unrelated Lamiaceae family also contains an alkaline alpha-galactosidase. This enzyme was partially characterized and found to have high affinity to stachyose. Also, leaves of the *Peperomia camptotricha L.* plant, from the family Piperaceae, show alpha-galactosidase activity at alkaline pH, suggesting that they also contain an alkaline alpha-galactosidase enzyme (Madore, M., "Catabolism of raffinose family oligosaccharides by vegetative sink tissues", In: Carbon Partitioning and Source-Sink Interactions in Plants, Madore, M. and Lucas, W. J. (eds.) pp. 204–214, 1995, American Society of Plant Physiologists, Maryland). This indicates the possibility that alkaline alpha-galactosidases, including novel enzymes not previously described, may function in other plants that metabolize galactosyl-saccharides, in addition to the cucurbits.

The use of an acidic form of alpha-galactosidase in biotechnological and industrial applications presents problems. For example, the use of an acidic form of alpha-galactosidase to remove the galactose-containing oligosaccharides, which include raffinose and stachyose, from soybean milk presents a dilemma, as described by Thanaunkul et al., ("Degradation of raffinose and stachyose in soybean milk by alpha-galactosidase from *Mortierella vinacea*"Jour. Food Science, 41:173–175, 1976). The pH of soybean milk, which is 6.2–6.4, is well above the optimum pH range of the *Mortariella vinacea* enzyme, which is 4.0–4.5, as shown using the natural substrate melibiose. Lowering the pH of the soybean milk solution to conform to the acidic enzyme's pH optimum caused the soybean proteins to precipitate and left a sour taste to the milk.

The use of alpha-galactosidase with an acidic pH optimum for the removal of raffinose from beet sugar faces a similar problem. In Suzuki et, 1969, ("Studies on the decomposition of raffinose by alpha-galactosidase of mold" Agr. Biol. Chem., 3–501–513, 1969) the pH of the beet molasses had to be lowered to 5.2 with sulfuric acid in order for the *Mortariella vinacea* enzyme to function.

Similarly, seroconversion of blood type B to blood type O would benefit from an alpha-galactosidase that is active at neutral to alkaline pH. since the described procedure (Goldstein et al., "Group B erythrocytes enzymatically converted to group O survive normally in A, B, and O individuals" Science, 215:168–170, 1982) requires the transfer of centrifuged erythrocytes to an acidic buffer in order for the enzyme to function. Lowering the pH to the optimum for the coffee bean alpha-galactosidase caused the cells to be less stable and lysis to occur. Thus, the seroconversion is carried out at pH 5.6, "reflecting a compromise between red cell viability and optimal alpha-galactosidase activity", as reported in Zhu et al. ("Characterization of recombinant alpha-galactosidase for use in seroconversion from blood group B to O of human erythrocytes", Archives of Biochemistry and Biophysics, 327:324–329,1996). Since the natural pH of blood is in the neutral to alkaline range (pH 7.3) alpha-galactosidase with activity in this pH range would have obvious advantages.

An additional limitation on the industrial utility of the currently available alpha-galactosidases is that their activity is frequently inhibited by the product of the reaction, galactose. As an example, the reported alkaline alpha-galactosidase from *Cucurbita pepo* leaves (Geaudreault, P. R. and Webb, J. A. "Partial purification and properties of an alkaline alpha-galactosidase from mature leaves of *Cucurbita pepo*", Plant Physiol., 71, 662–668, 1983) is strongly inhibited by alpha-galactose and it was calculated that 6.4 mM galactose reduced the reaction velocity by 50%.

Thus, there is a well-established need for an alpha-galactosidase with high activity at neutral to alkaline pH and with activity towards a broad spectrum of natural galactose-containing saccharides, particularly, but not exclusively raffinose.

SUMMARY OF THE INVENTION

The present invention seeks to provide a novel alkaline alpha-galactosidase which hydrolyzes a broad spectrum of galactose containing compounds, including, but not limited to, melibiose, raffinose, stachyose and guar gum. A novel form of alpha-galactosidase (E.C. 3.2.1.22, alpha-D-galactoside galacrohydrolase) was isolated from young melon fruit mesocarp tissue, purified to homogeneity, as determined by SDS-PAGE gel electrophoresis, and characterized. The enzyme is characterized by optimal activity at neutral to alkaline pH (7–8), together with a broader substrate specificity, as compared to previously reported alkaline alpha-galactosidases. At minimum, the enzyme hydrolyzes stachyose, raffinose and melibiose and guar gum. By contrast, a previously described alkaline alpha-galactosidase, which is quite specific for the tetrasaccharide stachyose, shows low activity toward, and low affinity for, the trisaccharide raffinose and no detectable activity against the disaccharide melibiose. The novel alkaline alpha-galactosidase enzyme of the present invention was purified using techniques of differential protein precipitation, ion-exchange chromatography, gel electrophoresis under native and denaturing conditions. Its native molecular weight is estimated as 84 kDa and its denatured molecular weight is estimated as 79 kDa. It is not a glycoprotein, as determined by the absence of binding to the lectin Concanavalin A. It shows relatively low affinity to the inhibitor galactose (Ki= 13 mM), together with relative insensitivity to the inhibitor. In particular, the enzyme has a high affinity for, and activity against the substrate raffinose.

These characteristics, particularly the neutral to alkaline activity optimum, together with the broad substrate specificity and most importantly the high affinity for raffinose, distinguish the enzyme from previously reported alpha-galactosidases. These very same characteristics, impart to this enzyme potential use in such diverse applications as the seroconversion of type B blood to type O blood, as well as a host of applications in the food products industry.

There is thus provided in accordance with a preferred embodiment of the present invention an enzyme isolated from an organism that metabolizes alpha-galactosyl containing saccharides, comprising an alpha-galactosidase (E.C. 3.2.1.22, alpha-D-galactoside galactohydrolase) with optimal activity in the neutral to alkaline pH range, and which hydrolyzes a variety of alpha-galactose containing saccharides, in particular raffinose. The enzyme is preferably a protein monomer and an exo-alpha-galactosidase.

In accordance with a preferred embodiment of the present invention the alkaline alpha-galactosidase is isolated from a plant that metabolizes alpha-galactosyl containing saccharides.

In accordance with a preferred embodiment of the present invention the alkaline alpha-galactosidase is derived from tissue of a member of the cucurbit family.

In accordance with a preferred embodiment of the present invention the alkaline alpha-galactosidase is derived from tissue of a melon plant.

Further in accordance with a preferred embodiment of the present invention the alkaline alpha-galactosidase is characterized by optimal activity in the range of pH 7–8.

Additionally in accordance with a preferred embodiment of the present invention the alkaline alpha-galactosidase is characterized by high affinity for the substrate raffinose and relatively low inhibition by galactose.

There is also provided in accordance with a preferred embodiment of the present invention a method for seroconversion of group B erythrocytes to group O erythrocytes, including providing an alkaline alpha-galactosidase which is hydrolytically active above about pH 7.0, and treating group B erythrocytes with the alkaline alpha-galactosidase so as to remove alpha-linked terminal galactose residues from the group B erythrocytes, thereby seroconverting the group B erythrocytes to group O erythrocytes.

There is also provided in accordance with a preferred embodiment of the present invention a method for reducing raffinose and stachyose levels in soybean milk.

There is also provided in accordance with a preferred embodiment of the present invention a method for reducing raffinose and stachyose levels in other plant products or tissues which contain these compounds.

There is also provided in accordance with a preferred embodiment of the present invention a method for modifying the rheological properties of galactose-containing gum products.

There is also provided in accordance with a preferred embodiment of the present invention a method for reducing raffinose levels in sugarbeet molasses thereby facilitating the crystallization of sucrose from said sugarbeet molasses.

BRIEF DESCRIPTION OF THE DRAWINGS

The present invention will be understood and appreciated more fully from the following detailed description. taken in conjunction with the drawings in which:

FIG. 6A illustrates the activity against the natural substrates raffinose (acid and alkaline Form I) or stachyose (alkaline Form II); FIG. 6B illustrates the activity against the synthetic substrate pNPG. The buffers used were citrate-phosphate (pH 4.0–7.0), HEPES-KOH (pH 7.0–8.0). and Tris (pH 8.0–8.5). All data were adjusted relative to maximum activity for each enzyme.

Figure 1:
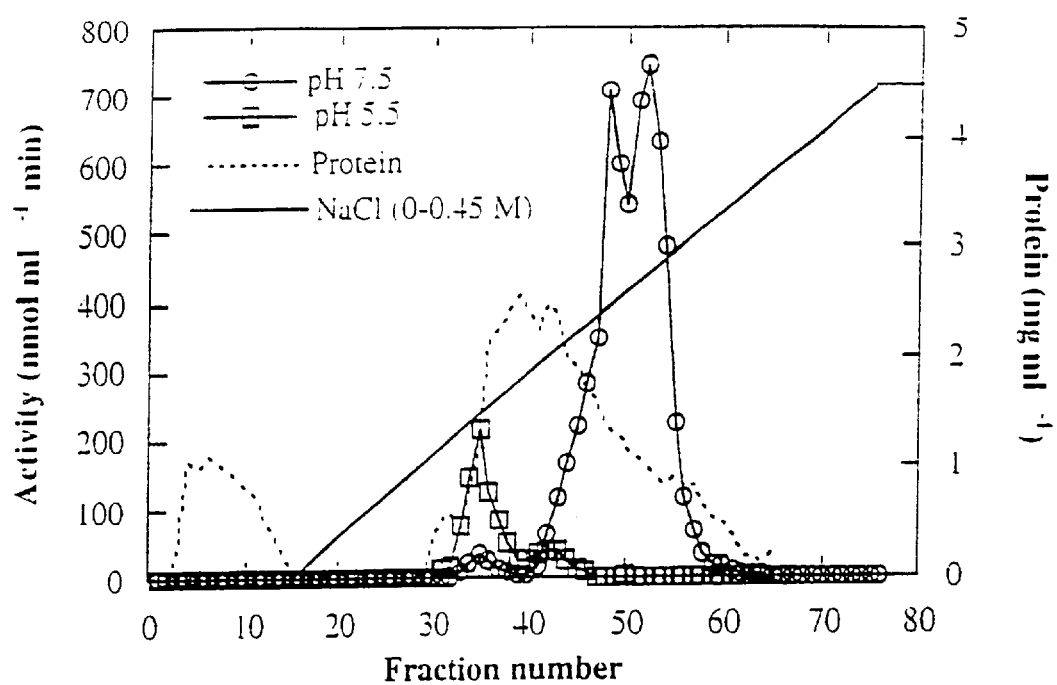
FIG. 1 is a simplified graphical illustration of separation of acid and alkaline alpha-galactosidases from melon fruit on ion-exchange chromatography, in accordance with a preferred embodiment of the present invention. The protein fraction of 5–50% (w/v) PEG-6000 was applied to a column of DEAE-Sepharose 4B and eluted with the indicated linear gradient of 0 to 0.45 M NaCl.

Table 1 illustrates the purification scheme for acid and alkaline I, II alpha-galactosidases from melon fruit. All the specific activities were assayed using raffinose (for acid and alkaline Form I) or stachyose (for alkaline Form II) as substrate.

Table 2 illustrates the comparison of the kinetic parameters ($K_m$, $V_{max}$ and $V_{max}/K_m$) of acid and alkaline Form I and Form II alpha-galactosidases from melon fruit, using the natural substrates raffinose, stachyose, and melibiose, and the synthetic substrate pNPG.

Table 3 illustrates the comparison of relatives activities of acid and alkaline Form I and Form II alpha-galactosidases from melon fruit using the substrates stachyose, raffinose and melibiose (each 10 mM) and guar gum (0.1%, w/v). Activity units for each enzyme was scaled so that the 1.00 value represents that enzymes activity on its preferred substrate.

Table 4 lists the partial amino acid sequences of two internal peptides, and the N-terminal peptide from the purified alkaline alpha-galactosidase.

DETAILED DESCRIPTION OF THE INVENTION

The present invention is now described in detail.

MATERIALS AND METHODS

Plants of muskmelon (*Cucumis melo* L.cv C-8 ) were crown under standard conditions in a greenhouse in Beit Dagan, Israel. Female flowers were hand pollinated and tagged at anthesis and fruit load was limited to 1 fruit per plant after 10 DAA (days after anthesis). For the study, of fruit development, primary fruits were harvested from 3 days prior to anthesis, at anthesis and 1, 2 4, 6, 10, 14, 20, 30 and 45 days after anthesis (DAA). Whole fruits before 6 DAA, and the inner mesocarp of the fruit tissues after 10 DAA, were thinly sliced and immediately frozen in liquid nitrogen prior to storage at −80 C. Chemicals and enzymes, unless specified otherwise, were purchased from Sigma and Boehringer, Mannheim, Germany.

Assays for Alpha-Galactosidase

For routine analysis and monitoring the activity in the purification steps, alpha-galactosidase was assayed as described by Smart and Pharr ("Characterization of alpha-galactosidase from cucumber leaves", Plant Physiology, 66:731–734, 1980), using p-nitrophenyl alpha-galactoside (pNPG) as substrate. Reaction was initiated by adding 50 ul enzyme aliquot to either 200 ul 100 mM pH 5.5 McIlvaine buffer or 100 mM pH 7.5 HEPES buffer, containing 5 mM pNPG at 35 C. The reaction was terminated after 10 min by adding 1 ml of 5% (w/v) $Na_2CO_3$ and activity expressed as nmol nitrophenol per min as measured at 410 nm. The hydrolysis of the natural substrates stachyose, raffinose or melibiose by alpha-galactosidases was measured with 10 mM substrate at pH 5.5 or 7.5 as in the assay with pNPG. The assay was started by adding 50 ul enzyme preparation at 35 C and terminated after 10 to 20 min by 2 min boiling. Rates of raffinose and stachyose hydrolysis were estimated by determining the amounts of galactose released, as described by Smart and Pharr (1980) using an enzyme-coupled reaction with NAD and galactose dehydrogenase (Boehringer Mannheim, E.C. 1.1.1.48).

Purification of Alpha-Galactosidases

In order to separate and characterize the various alpha-galactosidases present in melon fruit tissue an initial partial purification was carried out. Mesocarp tissue (200 g fresh weight) from 10 DAA fruit was homogenized in 200 ml chilled extraction buffer containing 50 mM HEPES-NaOH (pH 7.5), 2 mM $MgCl_2$, 2 mM EDTA and 5 mM DTT. The homogenate was filtered through four layers of cheese cloth and centrifuged at 18,000 g for 30 min. PEG-6000 was used to precipitate proteins from crude extract since there was a significantly irreversible loss of the activity when $(NH_4)_2SO_4$ was used. Precipitated proteins were collected from the 5–50% (w/v) PEG-6000 fraction, suspended in 50 ml buffer pH 7.5 containing 25 mM HEPES and 1 mM DTT (buffer A) and applied to an ion-exchange column (DEAE-Sepharose CL-6B, Pharmacia, 1.2×25 cm) previously equilibrated with buffer A. Unbound protein was eluted with buffer A and the bound protein was eluted at flow rate of 1 ml/min with a linear gradient of 0 to 0.45 M NaCl in buffer A. Fractions of 3.5 ml were collected and assayed for alpha-galactosidase activity at pH 5.5 or pH 7.5 with pNPG as substrate.

Purification of the Acid Form of Alpha-Galactosidase

For the partial purification of the acid form of alpha-galactosidase the fractions active at pH 5.5 were pooled and concentrated by reverse dialysis against solid sucrose. The concentrated fractions were chromatographed on a gel filtration column (Sephacryl-S 200, Pharmacia, 4.5×120 cm), previously equilibrated with buffer A, containing 0.15 M NaCl, at flow rate of 0.5 ml/min. Fractions of 3.5 ml were collected and assayed for alpha-galactosidase activity at pH 5.5, using pNPG as substrate. The active fractions were pooled and NaCl was added to a final concentration of 0.5 M prior to loading onto a lectin affinity column, (Concanavalin A-Sepharose 4B, 1×5 cm), previously equilibrated with buffer A containing 0.5 M NaCl. Unbound proteins were eluted with the same buffer and bound proteins were eluted with the same buffer containing 50 mM methyl alpha-D-glucopyranoside. The active fractions were then desalted by dialysis against buffer A for 12 h with two changes of the buffer. This enzyme fraction was used for the characterization of the acidic form of alpha-galactosidase.

Purification of Alkaline Alpha-Galactosidase

The fractions from the DEAE-Sepharose chromatography which were active at pH 7.5 were pooled and dialyzed against buffer A for 12 h prior to loading onto an HPLC ion exchange chromatography column (Mono-Q HR 5/5, Pharmacia), previously equilibrated with buffer A. Bound proteins were eluted with a linear gradient of 0.1 to 0.45 M NaCl and the active fractions were detected using pNPG as substrate at pH 7.5 as described above. Two peaks of alkaline alpha-galactosidase activity, labeled I and II, were separated by the Mono-Q chromatography. For the further purification of Form II the active fractions of the peak II were chromatographed on hydrophobic interaction chromatography. The tractions were pooled, brought to 1 M $(NH_4)_2SO_4$ and loaded on to a hydrophobic interaction column (phenyl-Sepharose CL-4B, 0.5×12 cm, Pharmacia) previously equilibrated with buffer A containing 1 M $(NH_4)_2SO_4$. The protein was eluted with a reverse stepwise gradient from 1 to 0 M $(NH_4)_2SO_4$ with 50 mini intervals in buffer A. Fractions containing the activity peak were collected and dialyzed for 12 h against buffer A and the dialysate was concentrated by reverse dialysis against solid sucrose. The enzyme, partially purified by hydrophobic interaction chromatography, was used for the characterization of Form II. The active fractions from the hydrophobic interaction column were further purified. Active fractions were separated electrophoretically using a Mini Prep Cell (Bio-Rad Laboratories, Hercules, Calif.) for discontinuous native-PAGE with 7% polyacrylamide, according to manufacturer's instructions. Fractions (0.25 ml/fraction) were assayed at pH 7.5 with pNPG as substrate for the activity. The active fractions were pooled, concentrated by Vivaspin Concentrator (Vivascience LTD, Lincoln, England), and run in a 8% SDS-PAGE. Proteins in the SDS-PAGE were identified using Coomassie Blue staining.

The hydrophobic interaction chromatography was not applied to the fractions of peak I as there was a great loss of the activity in $(NH_4)_2SO_4$ solution. Therefore, the active fractions from the Mono-Q column were used for the characterization of Form I. In addition, the Form I enzyme was further purified. as described in the following section.

Further purification of alkaline alpha-galactosidase Form I was carried out. The fractions of peak I, obtained after mono-Q chromatography, were chromatographed on a hydroxyapatite column (BioGel HTP, Bio-Rad, 0.5×12 cm) previously equilibrated with 10 mM Na-phosphate buffer pH 7.0 containing 0.5 mM DTT. The enzyme was eluted with a 60 ml linear 10 to 100 mM Na-phosphate gradient. The active fractions were pooled and concentrated by Vivaspin Concentrator. The concentrated protein was separated electrophoretically on a non-denaturing PAGE using the Mini-Protean II apparatus (Bio-Rad) using 1 mm thick slab gels containing 10% acrylamide, according to the procedure of Laemmli (1970). The active band was identified as a yellowish band in activity stain with 50 mM HEPES pH 7.5 containing 2 mM pNPG at 35 C. Following the native electrophoresis, the active band was excised, and the protein was eluted with $ddH_2O$ overnight and subjected to electrophoreses in 8% SDS-PAGE.

Amino Acid Sequencing

The Coomassie-stained band of purified alkaline alpha-galactosidase Form I was excised from the 8% SDS-PAGE gel and submitted for amino acid sequencing at the Protein Center of the Technion University, Haifa, Israel. The sequencing operation is as follows. Following gel destaining, the protein band was cut with a razor blade and the protein in it was reduced with DTT (5 mM) and carboxymethylated "in gel" using 10 mM iodoacetamide. The gel was then further destained in 50% acetonitrile with 100 mM ammonium bicarbonate, cut to little pieces and dried in vacuum. The gel pieces were rehydrated with 50 mM phosphate buffer pH8/100 mM ammonium bicarbonate pH 7.4/0.5 M tris-HCl pH 9.2 containing the protease (*S. aureus* V8 protease, Promega)/Lys-C protease (Boehringer)/ modified Trypsin (Promega). After an overnight incubation in 37 C. with shaking, the resulting peptides were eluted from the gel pieces with 60% acetonitrile with 0.1% TFA and analyzed by LC-MS as described below.

The peptides were resolved by reverse phase HPLC on a 1×150 mm Vydac C-18 column with a linear gradient of 4–65% acetonitrile in 0.025% TFA, at 1%/min at a flow rate of 40 ul/min. The flow was split post column: about 20% of the sample was microsprayed directly from the HPLC column into an electrospray iontrap mass spectrometer (LCQ, Finnigan) while 80% was collected manually into microfuge tubes for automated Edman sequencing. The mass spec analysis was done in the positive ion mode using repetitively a full MS scan followed by MS/MS experiment (collision induced fragmentation) on the most abundant ion selected from the mass scan. The MS and MS/MS data from the run was compared to the simulated proteolysis and fragmentation of the proteins in the "owl" database using the "Sequest" software (J. Eng and J. Yates, Univ. of Washington). Further identification of the protein was performed by sequencing peptides on the automated Sequencer (Perkin Elmer). Two peptide fragments, designated as P25 and P35 were sequenced by automated Edman degradation sequencing.

N-Terminal Peptide Sequencing

After resolving the purified alkaline alpha-galactosidase I on SDS-PAGE, as previously described, the protein was blotted to PVDF membrane (Immobilon-CD, Millipore Co.) using a Bio-Rad blotting apparatus. The transfer buffer contained 25 mM Tris, 192 mM Glycine, 20% methanol and 0.1 mM sodium thioglycolate. The N-terminal amino acid sequence of the purified alkaline alpha-galactosidase I was analyzed directly from the PVDF membrane using a Automatic Sequencer (Applied Biosystems), according to manufacturer's instructions.

Enzyme Properties

The optimum pH for each partially purified enzyme was determined using either 5 mM pNPG, 10 mM stachyose or 10 mM raffinose as substrates, in 100 mM McIlvaine buffer over a pH range of 4 to 7, or 100 mM HEPES buffer at pH range 7 to 8.5, at 35 C. The substrate specificity of the alpha-galactosidases was tested with pNPG, stachyose, raffinose, melibiose or guar gum (Sigma). Effects of galactose, fructose, glucose, sucrose, malate, citrate and of excessive stachyose, raffinose and pNPG on the enzyme activity were assessed. Km, Vmax values for pNPG, stachyose, raffinose or melibiose were determined by Lineweaver-Burk plots, as were Ki (inhibition) values for D-galactose inhibition.

Determination of the Native Molecular Mass and pI (Isoelectric Point)

The partially purified enzymes were chromatographed on a gel filtration column (Superdex 200 HR 10/30, Pharmacia Biotech., Uppsala, Sweden), equilibrated with 50 mM Na-phosphate buffer (pH 7.0) containing 0.15 M NaCl and 1 mM DTT. Retention time was compared to that of gel filtration markers (Sigma) for molecular weights 12 kDA to 200 kDA. The estimation of pI was carried out by isoelectric focusing (PHASTGEL IEF, Pharmacia Biotech., Uppsala, Sweden) on high speed gel electrophoresis (PHASTSYSTEMTM, Pharmacia Biotech., Uppsala, Sweden) at pH 4.0–6.5. Proteins were loaded to duplicate gels and focused according to the manufacturer's instructions. One of the gels was stained for protein using Coomassie Blue. The duplicate gel was sliced into 1 mm segment and assayed for enzyme activity using pNPG at pH 7.5. Standards with pI values of 4.55, 5.2 and 5.85 (Sigma) were used for comparison and the pI of the enzymes were estimated from the calibration curve and the distance of the active band from the anode.

SDS-PAGE (Polyacrylamide Gel Electrophoresis) and Nondenaturing PAGE

Denaturing SDS-PAGE was carried out using a Bio-Rad Mini-Protean II apparatus using 1 mm thick slab gels containing 8% acrylamide according to the procedure of Laemmli (1970). Gels were stained with Coomassie brilliant blue R-250 and destained in methanol: acetic acid: water solution. Molecular mass standards used (Pharmacia) were phosphorylase b (94 kD), albumin (67 kD), ovalbumin (43 kD), carbonic anhydrase (30 kD), trypsin inhibitor (20.1 kD), and alpha-lactalbumin (14.4 kD). Nondenaturing PAGE was run with 1 mm thick slab gels containing 10% acrylamide according to the procedure of Laemmli (1970). The active band was identified by incubating the gel in 5 nM pNPG in pH 7.5 HEPES buffer at 35 C. and then visualizing the yellow activity band.

Activities of Alpha-Galactosidases During Fruit Development

The activities of alpha-galactosidases in developing fruits were estimated in crude extracts with raffinose or stachyose as substrate at pH 5.5 or 7.5. Tissues were homogenized in a chilled mortar with 4 volumes of chilled extraction buffer containing 50 mM HEPES-NaOH (pH 7.5), 2 mM $MgCl_2$, 2 mM EDTA and 5 mM DTT. After centrifugation at 18,000 g for 30 min the supernatant was desalted with a 5 ml Sephadex G-25 column and used as the crude enzyme extract. Enzyme extracts from 10 g of 0 and 10 DAA fruits were also characterized after separation on a Mono-Q column. The 3 to 50% PEG-6000 (w/v) fraction from the above supernatant was separated on a Mono-Q HR 5/5 column previously equilibrated with buffer A, with a linear gradient of 0 to 0.45 M NaCl, as above. Active fractions were detected with the assays using pNPG as well as stachyose or raffinose as substrates at pH 5.5 and 7.5.

Protein Estimation

Protein was estimated according, to the method of Bradford (1976) using the BioRad protein assay and BSA as standard.

RESULTS

Purification of Alpha-Galactosidases

Figure 2:
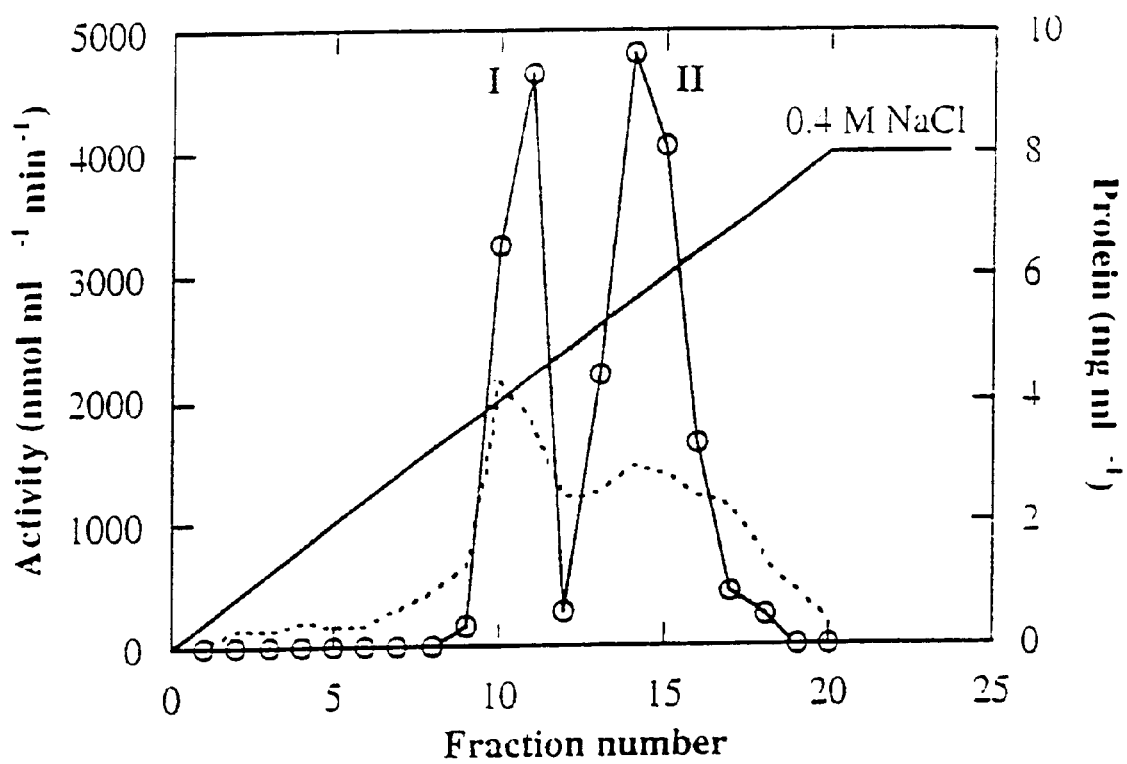
FIG. 2 is a simplified graphical illustration of separation of alkaline alpha-galactosidases forms I and II from melon fruit on ion-exchange chromatography, in accordance with a preferred embodiment of the present invention. The fractions active at pH 7.5, represented in FIG. 1, were pooled and applied to a HPLC Mono-Q column and eluted with the indicated linear gradient of 0 to 0.4 M NaCl.
Figure 3:
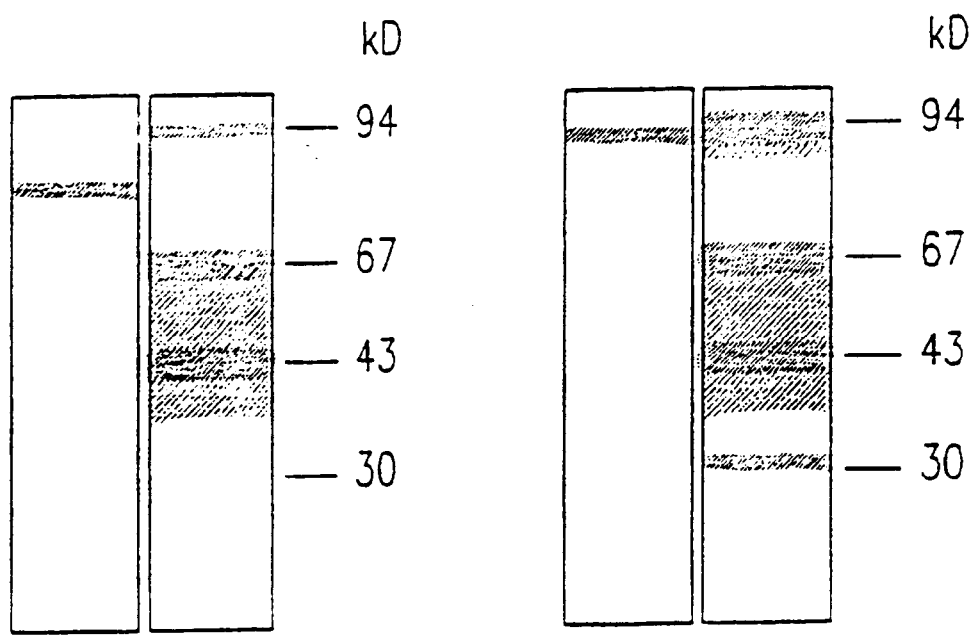
FIG. 3 shows a Coomassie blue-stained SDS-polyacrylamide gel electrophoresis (PAGE) gel showing the denatured alkaline alpha-galactosidase forms I (left) and II (right). Next to each of the purified proteins is a lane showing the separation of markers of known molecular weight, for comparison.

Three forms of alpha-galactosidase were resolved from young melon fruit mesocarp by DEAE-Sepharose ion exchange chromatography, in conjunction with Mono-Q chromatography, using pNPG as substrate (FIGS. 1 and 2). The first peak showed higher activity at pH 5.5 than at pH 7.5, while the latter two peaks both showed activity at pH 7.5 with little activity at pH 5.5. Accordingly, we referred the first peak as an acid form of alpha-galactosidase and the other two peaks as alkaline alpha-galactosidases Form I and Form II, respectively. The three enzyme forms were partially purified for the purpose of characterization (Table 1). Mono-Q ion exchange successfully resolved the two alkaline forms, and hydrophobic interaction chromatography was useful in the purification of alkaline Form II. After further purification, as described in Table 1, the two alkaline forms were elctrophoresed on a denaturing SDS-PAGE gel and a drawing of a photograph of two purified proteins is shown in FIG. 3. The acid alpha-galactosidase bound to Concanavalin A-Sepharose, indicating that it is a glycoprotein, and this was a useful step in its purification. Neither alkaline alpha-galactosidase forms I or II bound to Concanavalin A, suggesting that neither are glycoproteins. The purified enzymes were stable for at least 2 months when stored at −80° C.

Properties of Alpha-Galactosidases

Figures 4A, 4B, 4C:
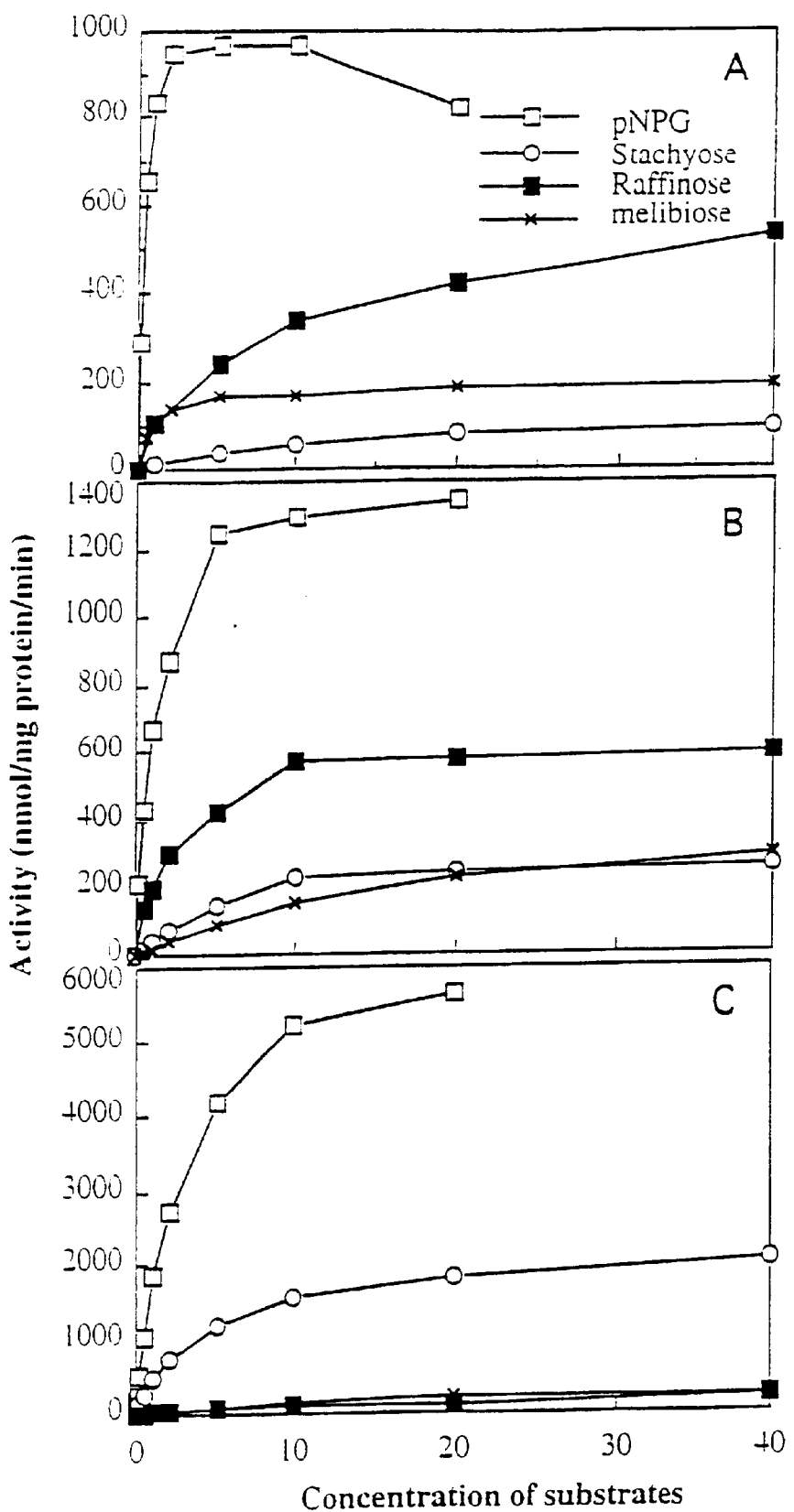
FIGS. 4A, 4B and 4C are simplified graphical illustrations of the kinetics of acid (FIG. 4A), alkaline I (FIG. 4B) and alkaline II (FIG. 4C) alpha-galactosidases with pNPG, stachyose, raffinose melibiose as substrate. The relative specificity of alkaline Form II for stachyose is evident, as compared to the broader specificity of alkaline alpha-galactosidase Form I.

The three enzymes are distinct with respect to their substrate specificity. The hydrolysis of the natural substrates, melibiose, raffinose and stachyose, were of particular interest to us. All three enzymes showed Michaelis-Menten kinetics at concentrations up to 40 mM melibiose, raffinose or stachyose (FIGS. 4A, 4B, 4C). Alkaline Form I exhibited nearly 2-fold higher activity, as well as higher affinity, to raffinose as compared to either melibiose stachyose. Nevertheless, there was significant activity towards melibiose and stachyose. In contrast, alkaline Form II was relatively specific to stachyose, with little activity toward raffinose or melibiose. The acid alpha-galactosidase exhibited a preferred specificity and higher activity with raffinose as compared to stachyose or melibiose.

The affinity constants (Km) and calculated maximal velocities (Vmax) for the substrates raffinose and stachyose, for each of the three alpha-galactosidases are summarized in Table 2. It can clearly be seen that the Form I alkaline enzyme is novel with respect to its relatively high affinity to both raffinose and stachyose, in distinction from the Form II alkaline enzyme, which is relatively specific to stachyose. The relative affinity constants (Km) of the two alkaline forms for the substrate raffinose is 1.5 and 26.3 for Forms I and II respectively.

The hydrolysis of guar gum, a complex polysaccharide with terminal alpha-galactose moieties, was also investigated. Guar gum (Sigma, 0.1% w/v) was incubated as substrate with the three enzyme fractions and the relative activity of galactose release was measured and is shown in Table 3. It can be seen that of the two alkaline forms only Form I shows significant activity towards guar gum.

Hydrolysis of the synthetic substrate pNPG did not give any indication of natural substrate specificity. The acid form showed the highest affinity for pNPG but highest maximal activity was observed with alkaline Form II, which had the lowest affinity to pNPG (Table 2). When using pNPG as substrate, the acid alpha-galactosidase was inhibited above 5 mM pNPG (FIG. 4A). The two alkaline forms followed Michaelis Menten kinetics up to substrate concentrations of 20 mM pNPG (FIGS. 2B, 2C).

Figures 6A, 6B:
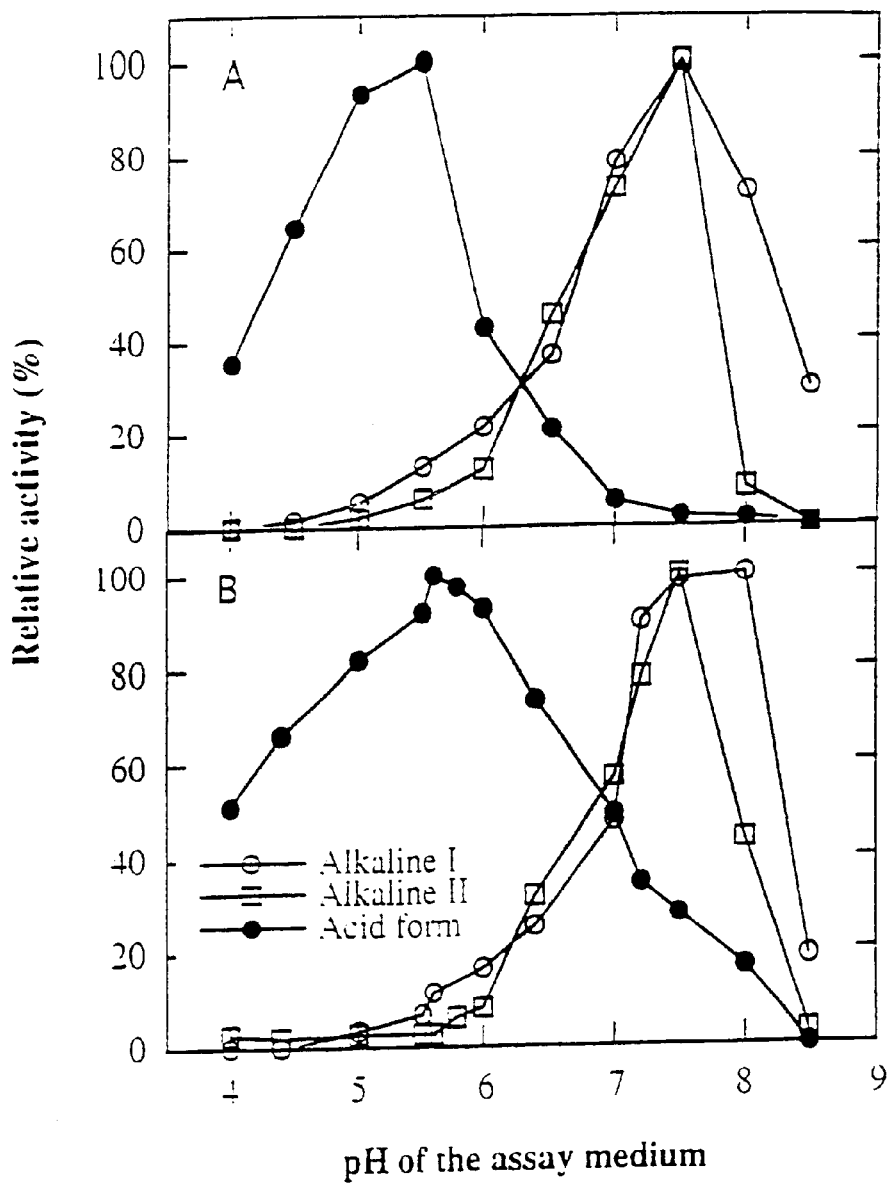
FIGS. 6A and 6B are simplified graphical illustrations of the effect of pH on activity of purified acid and alkaline alpha-galactosidases Form I and Form II.

The acid form exhibits a narrow pH range of maximal activity, between 5 and 5.5, with only approximately 5% of maximal activity at pH 7, when measured with its preferred substrate, raffinose (FIG. 6A). When using pNPG as substrate the acid form exhibited activity over a broad pH range, from 4 to 8, with maximal activity at 5.8 and approximately 35% maximal activity remaining at pH 7 (FIG. 6B). Both alkaline forms had maximal activity at pH 7.5 with raffinose and stachyose (for Form I and Form II, respectively), which was similar to that with pNPG as substrate. Form I retained high activity up to pH 8.3, while the activity of Form II declined already at lower pH and at pH 8.0 there was already little activity (FIGS. 6A and 6B).

TABLE 1

| Purification step | Activity nmol min$^{-1}$ | Protein mg | Specific activity nmol mg$^{-1}$ protein min$^{-1}$ | Yield % | Purification fold |
|---|---|---|---|---|---|
| Acid Form | | | | | |
| Crude extract | 13018 | 1152 | 11 | 100 | — |
| 5–50% PEG fraction | 11411 | 481 | 24 | 88 | 2 |
| DEAE-Sepharose | 4610 | 45 | 102 | 35 | 9 |
| Sephadex-200 | 2998 | 13 | 232 | 23 | 21 |
| Con-A | 1646 | 2.6 | 627 | 13 | 55 |
| Alkaline form I | | | | | |
| Crude extract | 27650 | 1152 | 24 | 100 | — |
| 5–50% PEG fraction | 20730 | 481 | 43 | 75 | 2 |
| DEAE-Sepharose | 9475 | 35 | 273 | 34 | 11 |
| Mono-Q | 7974 | 15 | 537 | 29 | 22 |
| Bio-gel HTP | 5103 | 3.7 | 1382 | 19 | 57 |
| Alkaline form II | | | | | |
| Crude extract | 18433 | 1152 | 16 | 100 | — |
| 5–50% PEG fraction | 16370 | 481 | 34 | 89 | 2 |
| DEAE-Sepharose | 10907 | 58 | 189 | 59 | 12 |
| Mono-Q | 8826 | 17 | 521 | 48 | 33 |
| Phenyl Sepharose 6FF | 5761 | 2.9 | 1973 | 31 | 123 |

Figures 4D, 4E, 4F:
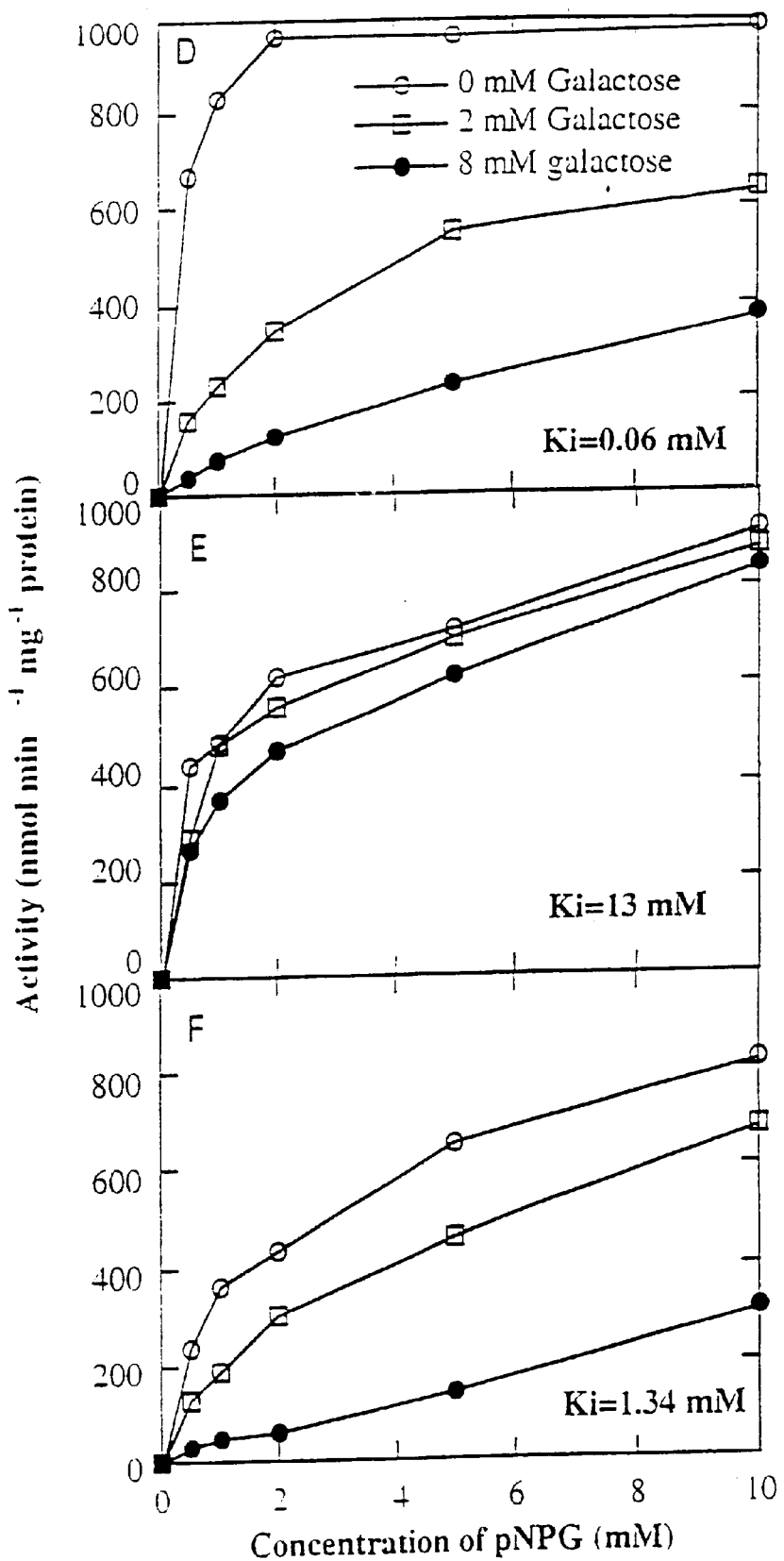
FIGS. 4D–F are simplified graphical illustrations of the kinetics of acid (FIG. 4D), alkaline I (FIG. 4E) and alkaline II (FIG. 4F) alpha-galactosidases with pNPG as substrate, in the presence of varying concentrations of the inhibitor galactose. The relative sensitivity of the acid form and the alkaline Form II for galactose is evident, as compared to the insensitivity of alkaline alpha-galactosidase Form I.

The inhibition of alpha-galactosidase activity by galactose is represented in FIGS. 4D–F. It can clearly be seen that the Form I alkaline enzyme is relatively insensitive to inhibition by galactose, as compared to the other forms. A galactose concentration of 8 mM, in the presence of 10 nM pNPG, caused a reduction of 65% and 70% in activity for the acid and Form II alkaline enzymes, respectively, but inhibited the activity of the alkaline Form I enzyme by a relatively insignificant 8%. The inhibition by galactose was characterized as "competitive" for all three enzymes, as determined by calculations from Lineweaver-Burke plots, with the acid form showing the strongest affinity for the inhibitor (Ki=0.06 mM galactose). The alkaline Form II also showed a strong affinity for the inhibitor (Ki=1.3 mM), as compared to the Form I enzyme which showed only low affinity for the inhibitor (Ki=13 mM galactose).

Figure 5:
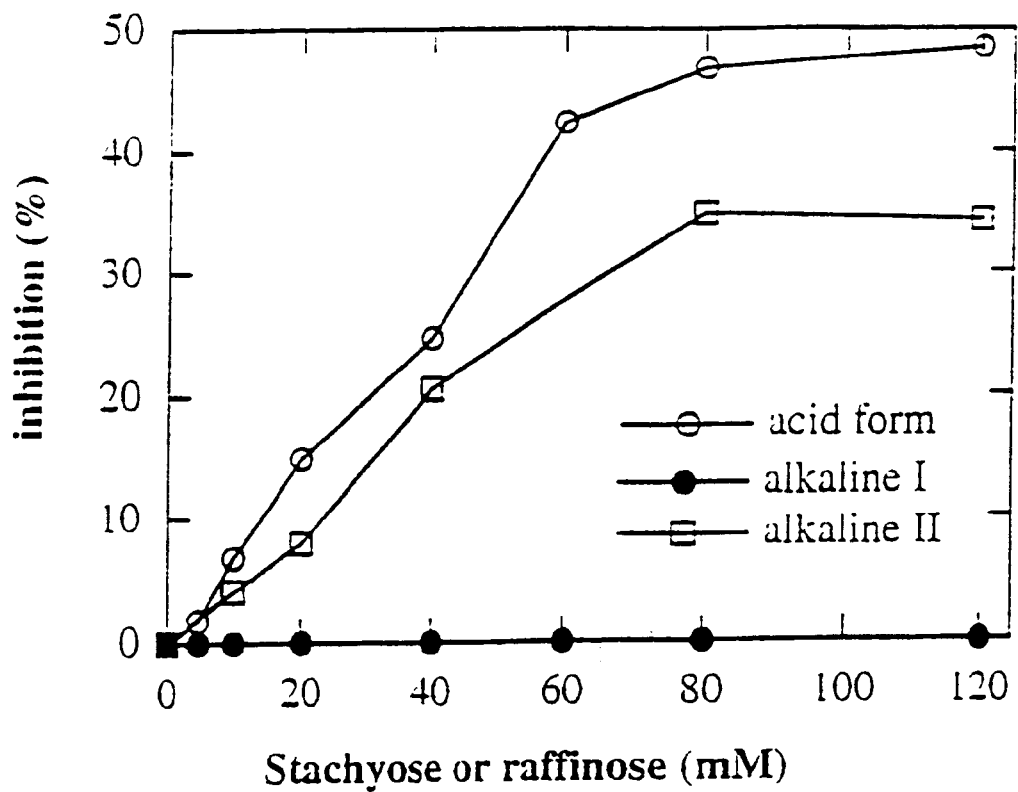
FIG. 5 is a simplified graphical illustrations indicating the extent of inhibition of the alpha-galactosidases by alternative substrates. In particular, it shows that the addition of excess raffinose (80 mM) to the assay medium containing 10 mM stachyose causes 35% inhibition of maximal alkaline Form II activity. The inhibition of the acid form by excess stachyose is demonstrated, particularly, that 80 mM stachyose added to the assay medium of the acid alpha-galactosidase causes 45% inhibition, as measure by the free galactose product. Of note is that alkaline Form I activity, as measured by the production of free galactose, does not decrease in the presence of excess stachyose.

There was an inhibitory interaction between the substrates raffinose and stachyose when either the acid form or the alkaline Form II were assayed (FIG. 5). For the alkaline Form II, addition of 80 mM raffinose to the assay medium containing 10 mM stachyose caused 35% inhibition of Form II activity, as measured by the release of galactose. For the acid form, 80 mM stachyose added to the assay medium of the acid alpha-galactosidase containing 10 mM raffinose caused a 45% inhibition in free galactose release. However, this inhibitory interaction was negligible for the alkaline Form I and the addition of excess amounts of stachyose did not lead to a decrease in released galactose.

Figure 7:
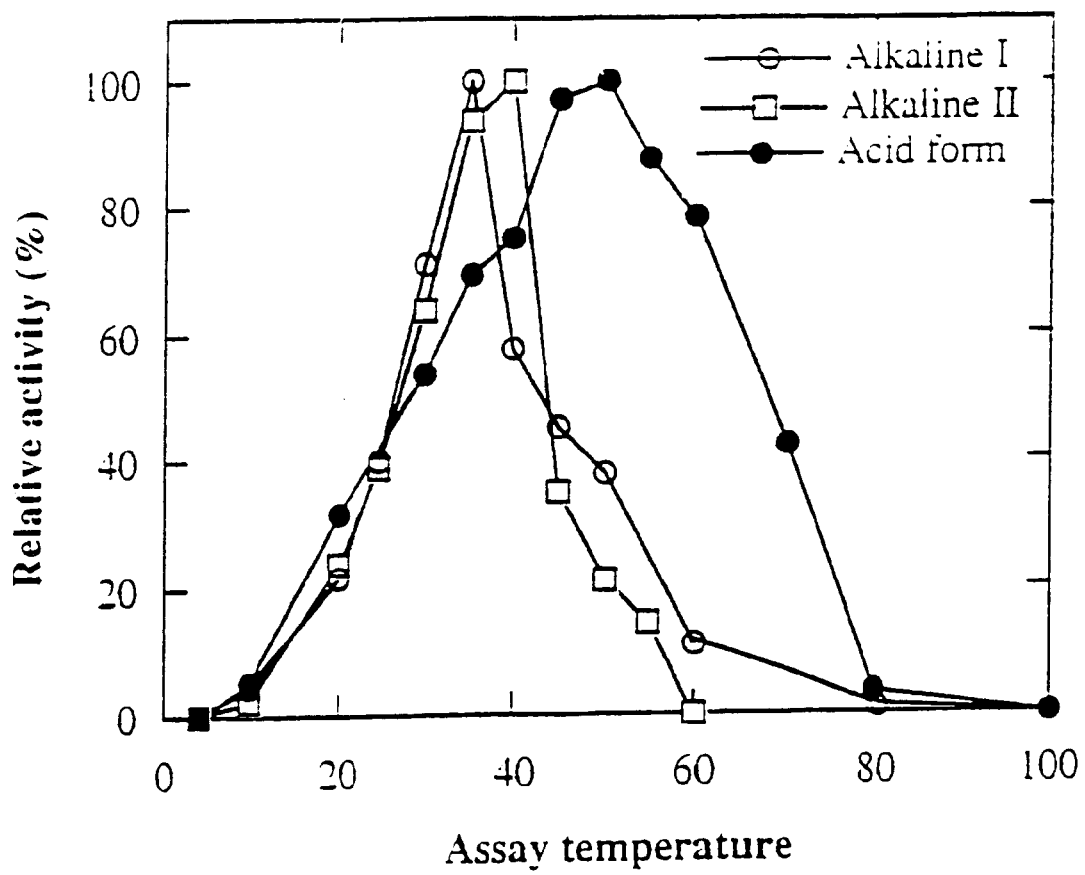
FIG. 7 is a simplified graphical illustration of the effect of reaction temperature on activity of partial purified acid and alkaline alpha-galactosidases I, II with pNPG as substrate. All data were adjusted relative to maximum activity for each enzyme.

Both alkaline forms I and II exhibited the highest activity in the temperature range of 35° to 40° C. and activity was significantly decreased above 40° C. (FIG. 7). The acid alpha-galactosidase was relatively thermophilic, with maximal activity at 50° C., and retained 40% of its activity at 70° C. (FIG. 5).

Figure 8:
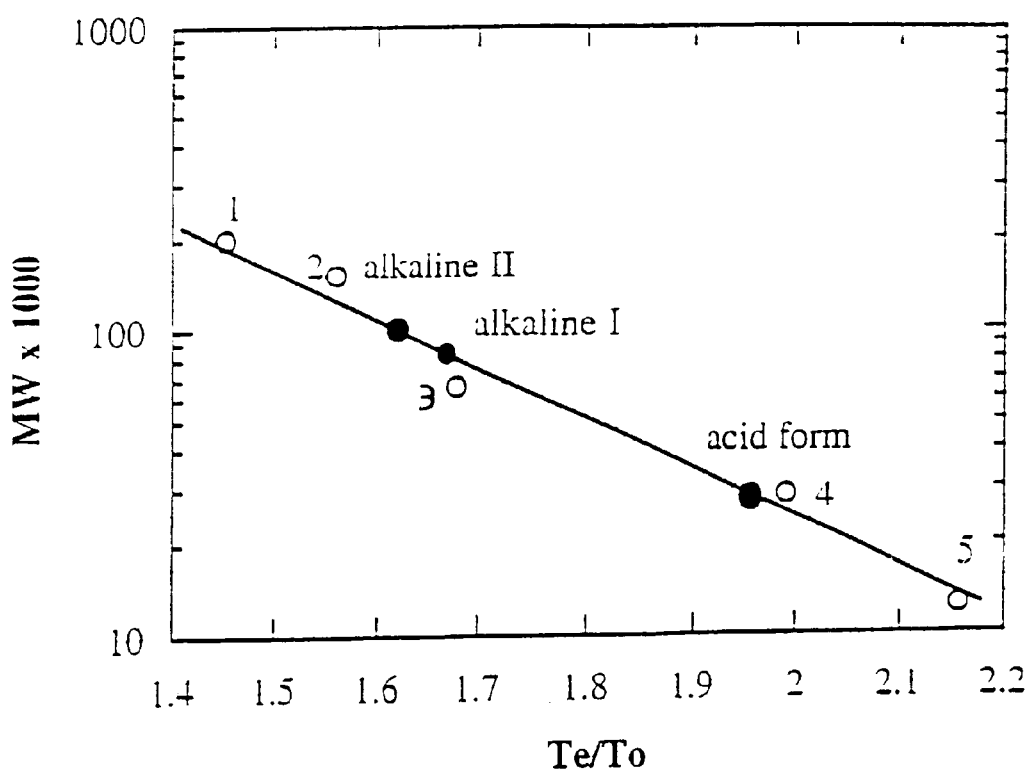
FIG. 8 is a simplified graphical illustration of the calibration curve from which the native molecular weight of the enzymes were determined (Sephacryl G-200).

The pI values of the two alkaline forms were estimated at 5.0 and 4.7 for the forms I and II, respectively, by activity staining of isoelectric focusing electrophoresis gels. The molecular weight of the denatured alkaline forms were estimated at 79 kDA and 92 kDA for Form I and II, respectively (FIG. 3). The molecular weight of the native proteins were 27, 84 and 102 kD for the acid form and alkaline Form I and Form II respectively (FIG. 8).

Changes of Acid and Alkaline Alpha-Galactosidases During Melon Fruit Development The substrate preferences (Table 2) and pH profiles (FIG. 6A) from the purified acid and Form I and Form II alkaline alpha-galactosidases allowed us to measure and estimate their activities even in crude extracts of melon fruit, using their natural substrates. Very little overlap in activity occurs between pH 5.5 and pH 7.5 (FIG. 4A) and, at pH 7.5, the activities of alkaline alpha-galactosidase I and II in the crude extracts could be distinguished by their respective activities when using raffinose or stachyose as substrate. The activity with raffinose at pH 7.5 is a good indicator of Form I activity since Form II is relatively specific for stachyose. There should be an overestimation of Form II activity when using stachyose due the hydrolysis of this substrate by Form I which is also present in the crude extract. Nevertheless, distinct developmental patterns of alpha-galactosidase activities are apparent when using these two substrates.

TABLE 2

| α-galactosidase | Substrate | Km (mM) | Vmax (unit*) | Vmax/Km |
|---|---|---|---|---|
| Acid form | Stachyose | 10.5 | 0.23 | 0.02 |
| | Raffinose | 4.2 | 0.71 | 0.17 |
| | Melibiose | 0.7 | 0.19 | 0.27 |
| | pNPG | 0.3 | 1.5 | 5.00 |
| Alkaline I | Stachyose | 4 | 0.24 | 0.06 |
| | Raffinose | 1.5 | 0.56 | 0.37 |
| | Melibiose | 20 | 0.3 | 0.02 |
| | pNPG | 1.2 | 1.4 | 1.17 |
| Alkaline II | Stachyose | 3.6 | 2.2 | 0.61 |
| | Raffinose | 26.3 | 0.28 | 0.01 |
| | Melibiose | 18.7 | 0.23 | 0.01 |
| | pNPG | 3 | 7.9 | 2.63 |

*unit: $\mu$mol mg$^{-1}$ protein min$^{-1}$

Figure 9:
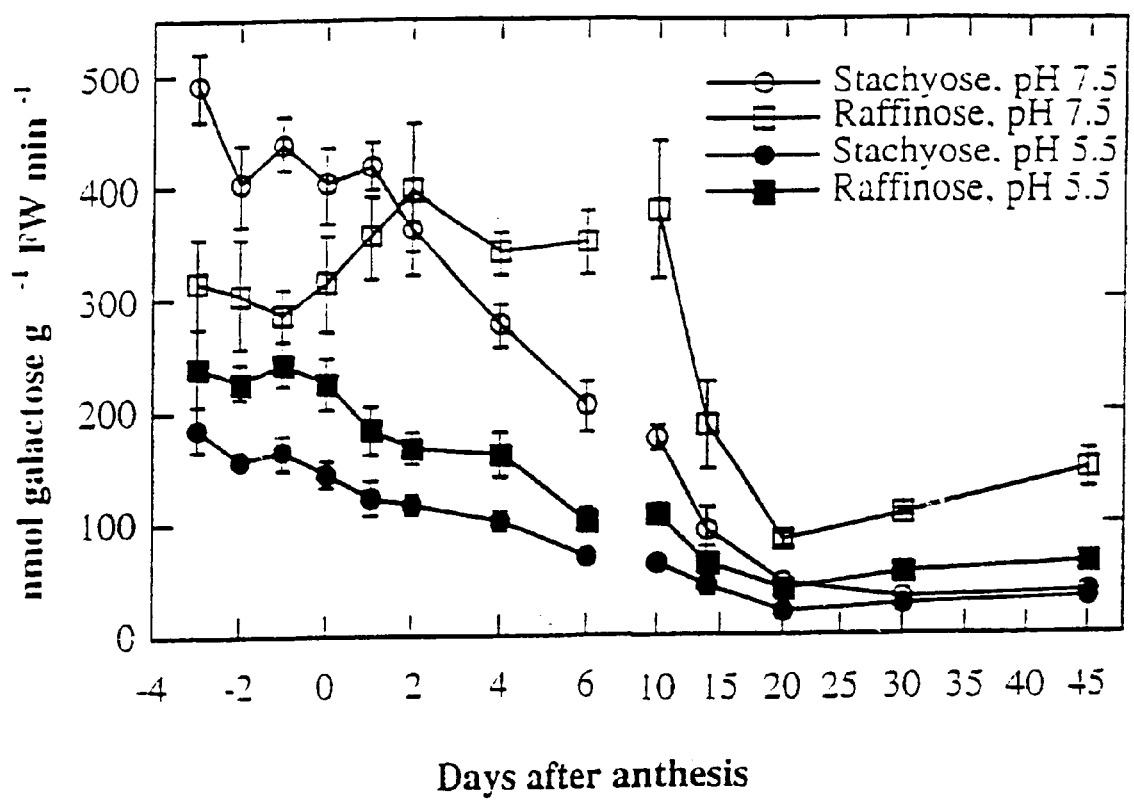
FIG. 9 is a simplified graphical illustration of activities of alpha-galactosidases during fruit development from ovary through maturation. Citrate-phosphate buffer pH 5.5 and HEPES buffer pH 7.5 were used for the assays with stachyose or raffinose as substrate. The activity at pH 5.5 with raffinose as substrate represents the acid form while the activities at pH 7.5 with raffinose or stachyose as substrate represent the alkaline alpha-galactosidase forms I and II, respectively. Data from fruit younger that 6 days after anthesis are from whole ovaries while only the mesocarp portion of the ovaries were sampled from fruit 10 days and older. Each value is the mean of results from four replicates each of which consisted of one fruit. Vertical bars represent standard errors.

Stachyose hydrolysis at alkaline pH was highest in the pre-anthesis fruit ovary and progressively declined through development (FIG. 9). Raffinose hydrolysis at alkaline pH (Form I), in comparison, increased during the pre-anthesis period and remained high during the initial fruit-setting period, declining only from 10 days after anthesis. The major alpha-galactosidase activity in the mature fruit was toward raffinose at alkaline pH. Raffinose and stachyose hydrolysis at acid pH also declined during fruit development but the relative hydrolysis of the two substrates remained the same at each stage measured (FIG. 9).

Partial amino acid sequence data was determined for the Form II enzyme as described earlier. Table 4 lists the amino acid sequence for two internal peptides and the N-terminal peptide. A comparison of the three peptide sequences against the SwissProt protein sequence database using the BLAST program did not reveal any meaningful homologies.

TABLE 3

| Substrate | Acid α-galactosidase | Alkaline α-galactosidase I | Alkaline α-galactosidase II |
|---|---|---|---|
| | Activity (unit) | | |
| Stachyose | 0.290 | 0.511 | 1.000 |
| Raffinose | 1.000 | 1.000 | 0.074 |
| Melibiose | 0.274 | 0.315 | 0.090 |
| Guargum | 0.328 | 0.181 | 0.032 |

In summary, although acid alpha-galactosidases often exist in multiple forms in leaves and seeds, only one form of alkaline alpha-galactosidase has been reported in plants in the prior art (Gaudreault and Webb 1983, 1986). In the present invention, three different alpha-galactosidases extracted from the fruit tissue of muskmelon are demonstrated, as resolved by ion-exchange chromatography (FIGS. 1 and 2). Two of the purified alpha-galactosidases exhibit maximum activity at neutral-alkaline conditions (FIG. 6). In addition to the pH optima, the two alkaline alpha-galactosidases show similar temperature sensitivity, and are non-glycosylated, in contrast to the acid alpha-galactosidase in melon fruit.

The purified acid form we studied is similar to the smaller molecular form of acid alpha-galactosidase isolated from cucumber leaves (Smart and Pharr, 1980), with respect to pH optima and Km for raffinose or stachyose. The alkaline alpha-galactosidase Form II which we report here appears similar to the previously reported alkaline alpha-galactosidase from squash leaves (Gaudreault and Webb, 1982, 1983), with respect to pH optima and affinity to stachyose and raffinose, as well as to inhibition by the product galactose.

The two alkaline alpha-galactosidases can be distinguished from one another by a number of characteristics, such as substrate affinities, pI, molecular weight and different inhibition by D-galactose and an interactive inhibition between the natural substrates, raffinose and stachyose. The most significant difference between the two alkaline forms is in their substrate preferences when hydrolyzing natural galactosyl-saccharides. The Form II enzyme is relatively specific for stachyose while the Form I shows preferred activity against raffinose, with significant activity against other galactose containing saccharides such as stachyose, melibiose and guar gum, as well.

It is a particular feature of the present invention that the Form I alkaline alpha-galactosidase has a high affinity for the substrate raffinose, as expressed in the enzyme's $Km_{raffinose}$ which is <5 mM.

Seroconversion of Group B Erythrocytes to Group O Erythrocytes

It is well established that group B erythrocytes can be enzymatically converted to group O erythrocytes in vitro by using a alpha-galactosidase enzyme. This is because the group B antigen differs structurally from the group O antigen only by the addition of one terminal alpha-linked galactose residue.

Such conversion is discussed in "Characterization of Recombinant alpha-Galactosidase for Use in Seroconversion from Blood Group B to O of Human Erythrocytes", A. Zhu et al., Archives of Biochemistry and Biophysics, 327:324–329, 1996. Acid alpha-galactosidase isolated from green coffee beans has been shown in the prior art to be highly active in removing the terminal alpha-linked galactose residues from the group B red cell surface. Similarly, the prior art shows that acid alpha-galactosidase enzymes from tomato fruit (Pressey, R., "Tomato Alpha-Galactosidase: Conversion of Human Type B Erythrocytes to Type O" Phytochemistry 23:55–48, 1984) and mung beans (Dey, P. M., "Characteristic Features of an Alpha-Galactosidase from Mung Beans", Eur. J. Biochem. 140:385–390) can each seroconvert type B erythrocytes to type O erythrocytes. In Zhu et al., a recombinant acid alpha-galactosidase from green coffee beans was produced in *Pichia pastoris*, a methylotrophic yeast strain, and recombinant alpha-galactosidase was purified from the *P. pastoris* culture supernatant by a simple chromatography procedure. The recombinant alpha-galactosidase was used to seroconvert group B erythrocytes to group O erythrocytes in vitro.

Seroconversion with the above described acid alpha-galactosidase enzymes has a severe disadvantage. These described alpha-galactosidase enzymes show optimum activity in the acidic pH range. For example, the enzyme described by Zhu et al. is acidic, displaying maximal activity at pH 6.4 toward the substrate pNPG, dropping sharply at pH's higher than 7.0 and having a second peak at pH 4.5. The optimal pH drops to between 3.6 and 4 if the substrate is melibiose, raffinose or stachyose. The removal of terminal alpha-linked galactose residues from the group B red cell surface by coffee bean alpha-galactosidase was observed when the pH was less than 6.0. However, the physiological pH of blood is about 7.3. Zhu et al. thus had to compromise and use recombinant alpha-galactosidase to treat red blood cells at pH 5.5. It is noted that the recombinant alpha-galactosidase exhibited a high activity at pH lower than 5.5, but the cells were less stable and began to lyse.

As described herein above, the alkaline alpha-galactosidase of the present invention is characterized by optimal activity at neutral to alkaline pH (7–8), in contrast to the prior art acid alpha-galactosidases. The enzyme of the present invention also features a broader substrate specificity, as compared to the prior art alkaline alpha-galactosidase. Accordingly, the alkaline alpha-galactosidase of the present invention may be used to seroconvert croup B erythrocytes of human blood to group O at the natural pH of human blood, and promises to be more effective than the enzymes used in the prior art since the enzyme's optimal pH encompasses the natural pH of human blood.

Examples of other uses of the alkaline alpha-galactosidase of the present invention are in the food industry. Certain legumes, such as soybean and its milk product, contain stachyose and raffinose which is metabolized in humans only by the microbial flora in the large intestine, thereby causing problems of flatulence. The pH of soybean milk is approximately 6.4 and cannot be lowered due to protein precipitation at a lower pH. However, the stachyose and raffinose may be efficiently hydrolyzed by the alkaline alpha-galactosidase of the present invention, thereby reducing significantly or eliminating altogether problems associated with digestion of these sugars.

Another use of the alkaline alpha-galactosidase of the present invention in the food industry, is in the enzymatic hydrolysis of the trisaccharide raffinose in sugar beet molasses to galactose and sucrose. The presence of raffinose in sugar beet molasses inhibits the crystallization of the commercially important sucrose in the molasses. The hydrolysis of the raffinose to galactose and sucrose facilitates the crystallization of the sucrose.

Another use of the alkaline alpha-galactosidase of the present invention in the food industry, is in the enzymatic modification of plant gums, such as guar gum. The prior art (Bulpin et al., "Development of a biotechnological process for the modification of galactomannan polymers with plant alpha-galactosidase" Carbohydrate Polymers 12:155–168, 1990) has shown that the modification of guar gum by alpha-galactosidase modifies the rheological and stabilization properties of the gum, making it similar to the more functional and more expensive locust bean gum.

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

TABLE 4

| Peptide | Amino acid sequences | |
| --- | --- | --- |
| P-25 | EYPIQSPGNVSNL | (SEQ. ID No. 1) |
| P-35 | DISLTE(R/L)VT | (SEQ. ID No. 2) |
| N-terminal | TVGAGITISDANLTVLG | (SEQ. ID No. 3) |

What is claimed is:

1. An isolated enzyme from a plant of the Cucurbit family comprising,
   a) an alpha-galactosidase (E.C. 3.2.1.22, alpha-D-galactoside galactohydrolase) activity;
   b) a $K_m$ for the substrates raffinose of less than about 10 mM;
   c) optimal activity in the range of pH 7.0 to pH 8.0;
   d) molecular mass of about 84 kDa, as determined by gel electrophoresis;
   the enzyme being non-glycosylated.

2. An enzyme according to claim 1 wherein said $K_m$ for the substrate raffinose is less than about 5 mM.

3. An enzyme according to claim 1 wherein said $K_m$ for the substrate raffinose is less than or equal to about 1.5 mM.

4. An enzyme according to claim 1 wherein said plant is a melon plant.

5. An enzyme according to claim 1 isolated from the fruit tissue of the plant.

6. An enzyme according to claim 1 wherein said enzyme is a protein monomer.

7. An enzyme according to claim 1 wherein said enzyme is an exo-alpha-galactosidase.

8. A method for removing alpha-galactose from galactosyl-saccharide containing material comprising:
   a) providing an enzyme of claim 1; and,
   b) contacting said enzyme with said galactosyl-saccharide containing material so as to remove alpha-galactose from said galactosyl-saccharide containing material.

9. An isolated plant enzyme having,
   a) an alpha-galactosidase (E.C. 3.2.1.22, alpha-D-galactoside galactohydrolase) activity;
   b) a $K_m$ for the substrates raffinose of less than about 10 mM;
   c) optimal activity in the range of pH 7.0 to pH 8.0;
   d) molecular mass of about 84 kDa, as determined by gel electrophoresis;
   the isolated plant enzyme being non-glycosylated and having an N-terminal sequence as set forth in SEQ. ID. NO: 3.

10. An isolated plant enzyme of claim 9 wherein said $K_m$ for the substrate raffinose is less than about 5 mM.

11. An isolated plant enzyme of claim 9 wherein said $K_m$ for the substrate raffinose is less than or equal to about 1.5 mM.

12. An isolated plant enzyme of claim 9 isolated from an alpha-galactosyl saccharide metabolizing plant.

13. An isolated plant enzyme of claim 12 wherein said plant is a member of the Cucurbit family.

14. An isolated plant enzyme of claim 13 wherein said plant is a melon plant.

15. An isolated plant enzyme of claim 9 wherein said enzyme is isolated from the fruit tissue of the plant.

16. An isolated plant enzyme of claim 9 wherein said enzyme is a protein monomer.

17. An isolated plant enzyme according to claim 9 wherein said enzyme is an exo-alpha-galactosidase.

18. A method for removing alpha-galactose from galactosyl-saccharide containing material comprising:
   a) providing an isolated plant enzyme of claim 9; and,
   b) contacting said enzyme with said galactosyl-saccharide containing material so as to remove alpha-galactose from said galactosyl-saccharide containing material.

* * * * *